United States Patent [19]

Yamazaki et al.

[11] 4,339,590
[45] Jul. 13, 1982

[54] CYCLIC SULFUR COMPOUNDS

[75] Inventors: Noboru Yamazaki, Tokyo; Seiichi Nakahama, Toyohama; Kazuo Yamaguchi, Mitaka, all of Japan

[73] Assignee: Japan Synthetic Rubber Company, Limited, Tokyo, Japan

[21] Appl. No.: 226,834

[22] Filed: Jan. 21, 1981

[30] Foreign Application Priority Data

May 21, 1980 [JP] Japan ............................ 55-66346

[51] Int. Cl.³ .......................................... C07D 341/00
[52] U.S. Cl. ..................................................... 549/11
[58] Field of Search ......................................... 549/11

[56] References Cited

U.S. PATENT DOCUMENTS 2,715,635 8/1955 Davis ..................................... 549/11

Primary Examiner—Richard Raymond
Attorney, Agent, or Firm—Oblon, Fisher, Spivak, McClelland & Maier

[57] ABSTRACT

A cyclic sulfur compound represented by the formula,

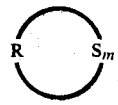

wherein R is $-(CH_2CH_2O)_n-CH_2CH_2-$, m is an integer of 2 to 4 and n is an integer of 1 to 3 is novel and can be used as a crosslinking agent instead of sulfur per se and also as a monomer for preparing polysulfide polymer. Said cyclic sulfur compound can be produced by reacting a metal sulfide represented by the formula,

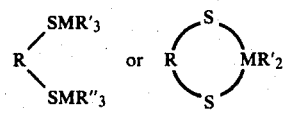

wherein R is the same as defined above, R' and R" are independently selected from alkyl groups and aryl groups and M is silicon or tin, with a halogen, sulfur dichloride or sulfur monochloride.

6 Claims, 13 Drawing Figures

CYCLIC SULFUR COMPOUNDS

BACKGROUND OF THE INVENTION

1. Field of the Invention

This invention relates to a cyclic sulfur compound (cyclic polysulfide), and more particularly, to a cyclic sulfur compound represented by the formula, (I)

wherein R is $-(CH_2CH_2O)_n CH_2CH_2-$, m is an integer of 2 to 4 and n is an integer of 1 to 3, and a process for producing the same.

2. Description of the Prior Art

Cyclic sulfur compounds containing at least two sulfur atoms are not so much present in nature. However, these are known Nereistoxin which is the toxin of *Lumbriconereis heteropoda* (a kind of marine animal), Lenthionine which is the fragrant ingredient of *Cortinellus shiitake*, 1,2,4,6-tetrathiepane contained in *Chondria californica* of red alga which exhibits antibacterial and antifungous activities, and the like. Attention is directed to a cyclic sulfur compound as one of the compounds having a physiological activity. In addition, in view of its position in organic industrial chemistry, the cyclic sulfur compound can be utilized as a crosslinking agent instead of sulfur per se or as a monomer for preparing a polysulfide polymer having good resistance to weather and oil.

Cyclic sulfur compounds represented by the formula (I) wherein R consists of a hydrocarbon (CH) have already been known, and the following synthesis methods have been known:

(1) Davis et al's method [F. O. Davis and E. M. Fettes, J. Am. Chem. Soc., 70, 2611 (1948)],
(2) Affleck et al's method [J. G. Affleck and G. Dougherty, J. Org. Chem., 15, 865 (1950)],
(3) Cragg et al's method [R. H. Cragg and A. F. Weston, Tetrahedron Letters, 655 (1973)],
(4) Swan et al's method [B. Milligam and J. M. Swan, J. Chem. Soc., 2901 (1965)],
(5) Harpp et al's method [D. N. Harpp, K. Stelion and T. H. Cham, J. Am. Chem. Soc., 100, 1222 (1978); J. A. Moore, J. E. Kelly, D. N. Harpp and T. G. Back, Macromolecules, 10, 718 (1977)],
(6) Harpp et al's method [D. N. Harpp and Alessandro Granata, J. Org. Chem., 44, 4144 (1979)], and the like.

The present inventors have paid their attention to the fact that such silyl sulfides as used in the Abel et al reaction [E. W. Abel and D. A. Armitage, J. Chem. Soc., 5975 (1964)] and such tin sulfides as used in the Wardell et al reaction [J. L. Wardell and P. L. Clarke, J. Organometal Chem., 26, 345 (1971)] have a high reactivity in view of the fact that in the Abel et al reaction, dibutyl disulfide is obtained in high yield by the reaction between butylthiotrimethyl silane and bromine and that in the Wardell et al reaction, di-4-toluyl tetrasulfide is obtained in high yield by the reaction between tripropyltin-4-toluyl sulfide and sulfur monochloride, and have conducted extensive research on the synthesis of cyclic sulfur compounds to find a novel process for producing novel cyclic sulfur compounds in high yield.

SUMMARY OF THE INVENTION

According to this invention, there is provided novel cyclic sulfur compounds represented by the formula, (I)

wherein R is $-(CH_2CH_2O)_n CH_2CH_2-$, m is an integer of 2 to 4 and n is an integer of 1 to 3.

This invention further provides a novel process for producing a cyclic sulfur compound represented by said formula (I), which comprises reacting (A) a metal sulfide represented by the formula, (II)

or

(III)

wherein R is the same as defined above, R' and R" are independently selected from the group consisting of alkyl groups and aryl groups, M is silicon or tin, with (B) a halogen, sulfur dichloride or sulfur monochloride.

DETAILED DESCRIPTION OF THE INVENTION

The reactions in the present process can be schematically shown by the following formulas:

In the formulas (II) and (III), R represents $-(CH_2CH_2O)_n CH_2CH_2-$ as defined above as to the formula (I), and R' and R" are independently selected from the group consisting of alkyl groups and aryl groups, the representatives of which are methyl, ethyl, propyl, butyl, hexyl, octyl, phenyl, tolyl, naphthyl and the like.

As the halogen to be reacted with the reactant (A), bromine, chlorine and the like may be used, and bromine is particularly preferred.

The reactant (A), namely a metal sulfide, can be prepared, for example, by reacting a dithiol represented by the formula, $$HS(CH_2CH_2O)_{\overline{n}}CH_2CH_2SH$$

with a trialkylchlorosilane or a trialkylchlorotin represented by the formula, $$R'_3SiCl \text{ or } R'_3SnCl,$$

to prepare a metal sulfide represented by the formula (II), or by reacting said dithiol with a dialkyldichlorosilane or a dialkyldichlorotin represented by the formula, $$R'_2SiCl_2 \text{ or } R'_2SnCl_2$$

to prepare a metal sulfide represented by the formula (III).

The yield of the cyclic sulfur compound is varied depending upon the production conditions, and the generally preferable synthesis method is the case where the metal sulfide is a silicon sulfide, in which case the yield is high and the isolation of the cyclic sulfur compound is easy.

The cyclic sulfur compound of this invention can be synthesized in an aliphatic hydrocarbon solvent such as hexane, heptane, or the like; an alicyclic hydrocarbon solvent such as cyclohexane or the like; a mixture of the two; or a polar solvent such as dioxane, carbon tetrachloride, dichloroethylene, trichloroethylene, tetrahydrofuran or the like. Tetrahydrofuran and carbon tetrachloride are preferably used as the solvent.

The reaction temperature is not critical, and it may be the refluxing temperature of the solvent or as low as the dry ice temperature (−75° C.).

The concentrations of the reactants are not critical, and the reaction may be effected at any reactant concentrations.

When the cyclic sulfur compound of this invention is used as a crosslinking agent in a rubber, the rate of dispersion of the cyclic sulfur compound in the rubber is higher than that of sulfur per se and the resulting dispersion is uniform. Even when the rubber compound containing the cyclic sulfur compound is subjected to vulcanization at a high temperature for a long period of time, no reversion occurs. In addition, the cyclic sulfur compound is difficult to bleed in the vulcanizate.

That the reaction product is a cyclic sulfur compound (cyclic polysulfide) and not a linear polysulfide can be confirmed by an ultraviolet absorption spectrum (UV spectrum) analysis, an infrared absorption spectrum (IR spectrum) analysis, a nuclear magnetic resonance spectrum (NMR spectrum) analysis, a mass spectrometric analysis and the like.

The UV spectrum is used to determine whether the sulfur-sulfur linkage is of the straight chain type or the branched chain type. The IR spectrum is used to confirm the absence of the thiol which appears where the ring has not been formed from the metal disulfide. The NMR spectrum is used to confirm that the reaction product is a cyclic sulfur compound based on the fact that the shift of H of —CH$_2$— in the cyclic structure is different from the shift of H in the straight chain structure. The mass spectrometric analysis is used to measure the molecular weight of the reaction product. The molecular weight and elementary analysis values of the reaction product as measured were relatively well accorded with those obtained by calculation from the cyclic sulfur compound determined theoretically.

BRIEF DESCRIPTION OF THE DRAWINGS

This invention is further explained below referring to Examples and the accompanying drawings, in which

FIG. 6 is the IR spectrum of 1,2,3-trithia-6-oxacyclooctane produced in Example 2.

DESCRIPTION OF PREFERRED EMBODIMENTS

EXAMPLE 1

1,2,3-Trithia-6,9,12-trioxatetradecane represented by the formula, could be synthesized by reacting α,ω-3,6,9-trioxaundecanedithiol with trimethylchlorosilane to which a compound represented by the formula, wherein R is —(CH$_2$CH$_2$O)$_3$CH$_2$CH$_2$—, and then reacting said compound (V) with sulfur dichloride (SCl$_2$).

In a 200-ml 2-necked flask equipped with a dropping funnel, which flask had been sufficiently dried and subjected to nitrogen-substitution, was placed 80 ml of anhydrous tetrahydrofuran which had previously been treated with metallic sodium and aluminum lithium hydride. Subsequently, 1.72 mmols of the compound (V) was added to the flask and the resulting mixture was well stirred to prepare a solution of the compound (V) in tetrahydrofuran. To this solution was added dropwise a solution of 1.8 mmols of sulfur dichloride in 10 ml of anhydrous tetrahydrofuran through the dropping funnel to effect reaction. The above procedures were conducted under a nitrogen atmosphere. The dropwise addition was started after the flask was sufficiently cooled in an ice bath, and the ice bath was removed after the completion of the dropwise addition, after which stirring was effected at room temperature for 24 hours. After the completion of the reaction, about 70 ml of the tetrahydrofuran was recovered by distillation under reduced pressure, and the resulting concentrated reaction mixture was subjected to a liquid chromatography to separate the product. The yield of the objective 1,2,3-trithia-6,9,12-trioxatetradecane was 61%, and the identification of said compound was effected by an ultraviolet absorption spectrum analysis, an infrared absorption spectrum analysis, a nuclear magnetic resonance spectrum analysis and a mass spectrometric analysis.

Figure 1:
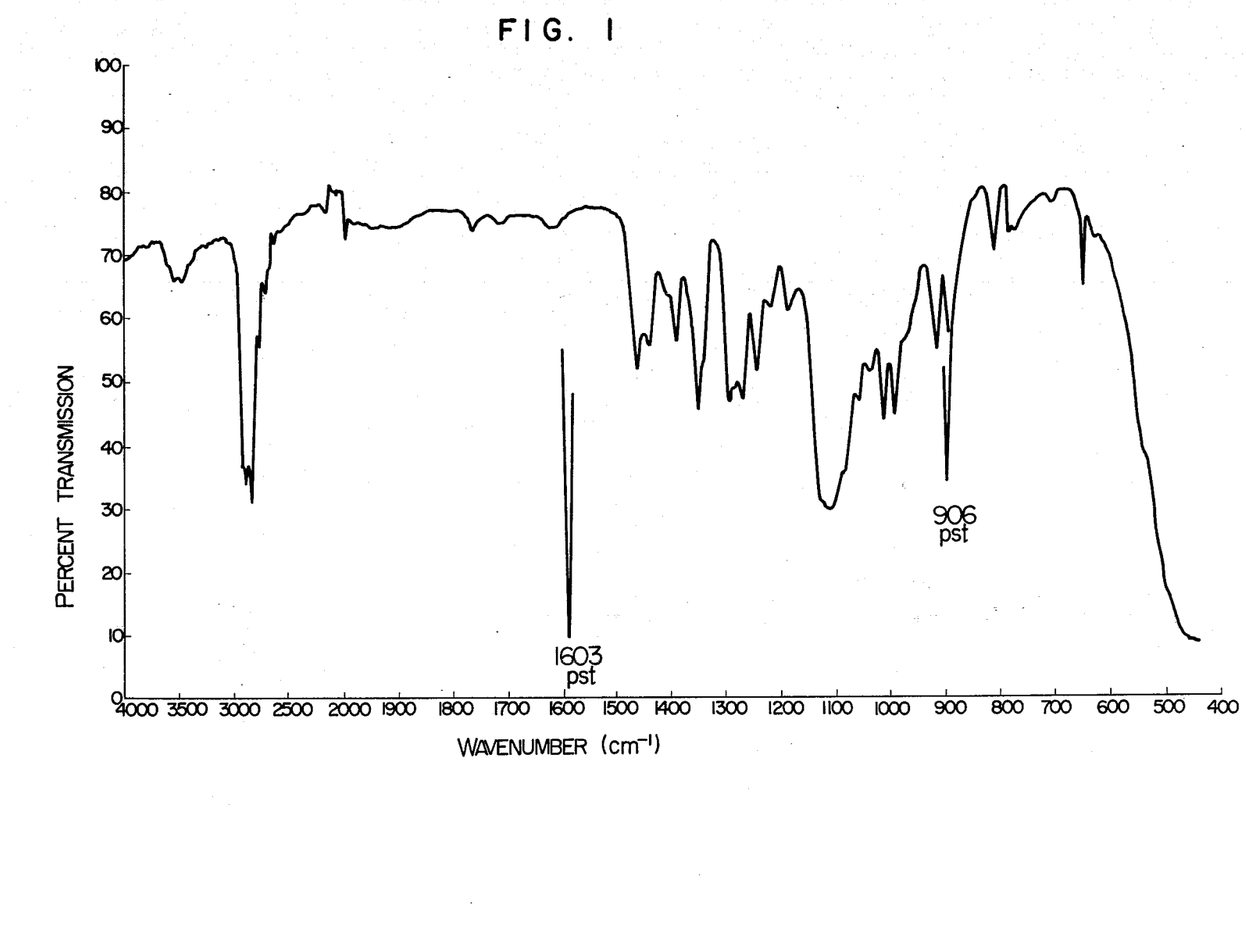
FIG. 1 is the IR spectrum of 1,2,3-trithia-6,9,12-trioxatetradecane produced in Example 1.
Figure 2:
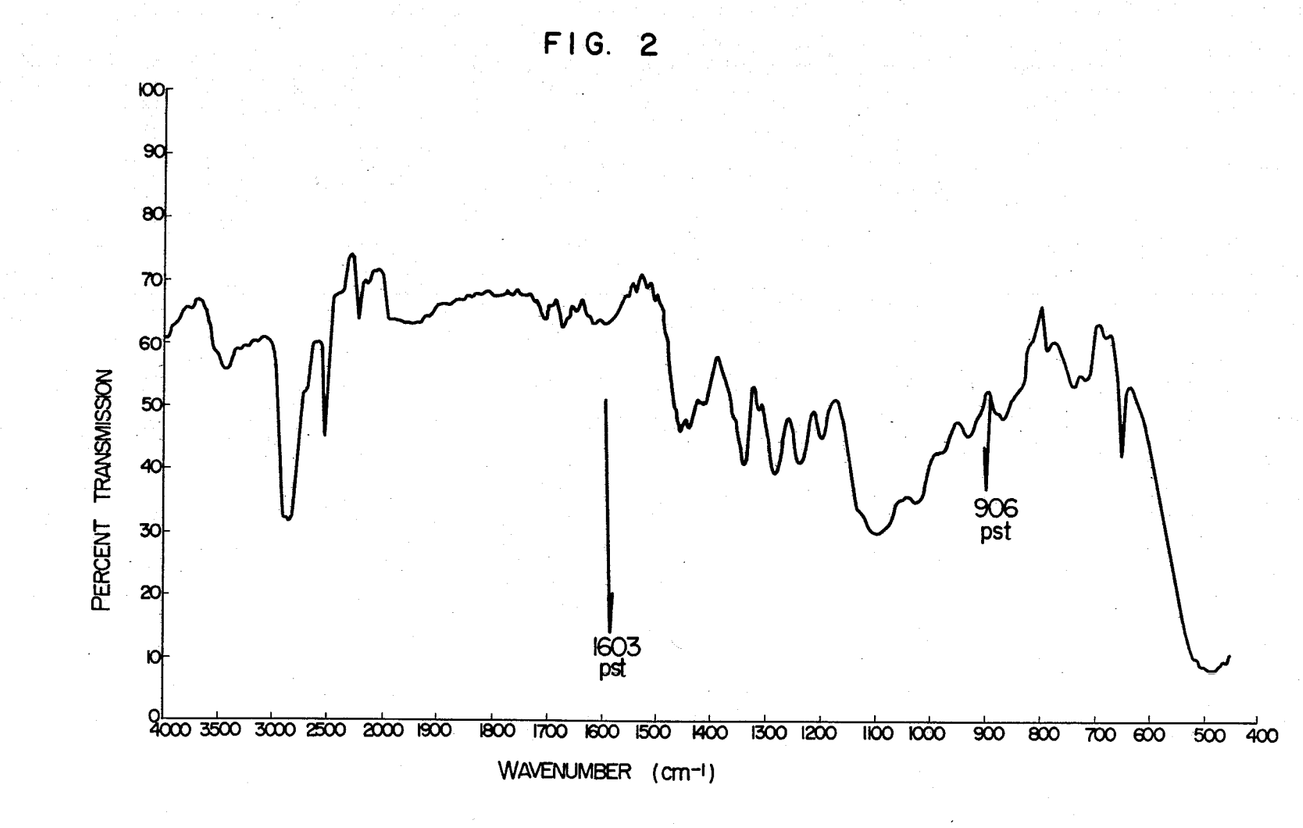
FIG. 2 is the IR spectrum of α,ω-3,6,9-trioxaundecanedithiol.

The IR spectrum of the reaction product is shown in FIG. 1. From the IR spectrum of the starting $\alpha,\omega$-3,6,9-trioxaundecanedithiol shown in FIG. 2, it can be seen that —SH is absent in the reaction product (absorption at 2,500–2,600 cm$^{-1}$).

Figure 3:
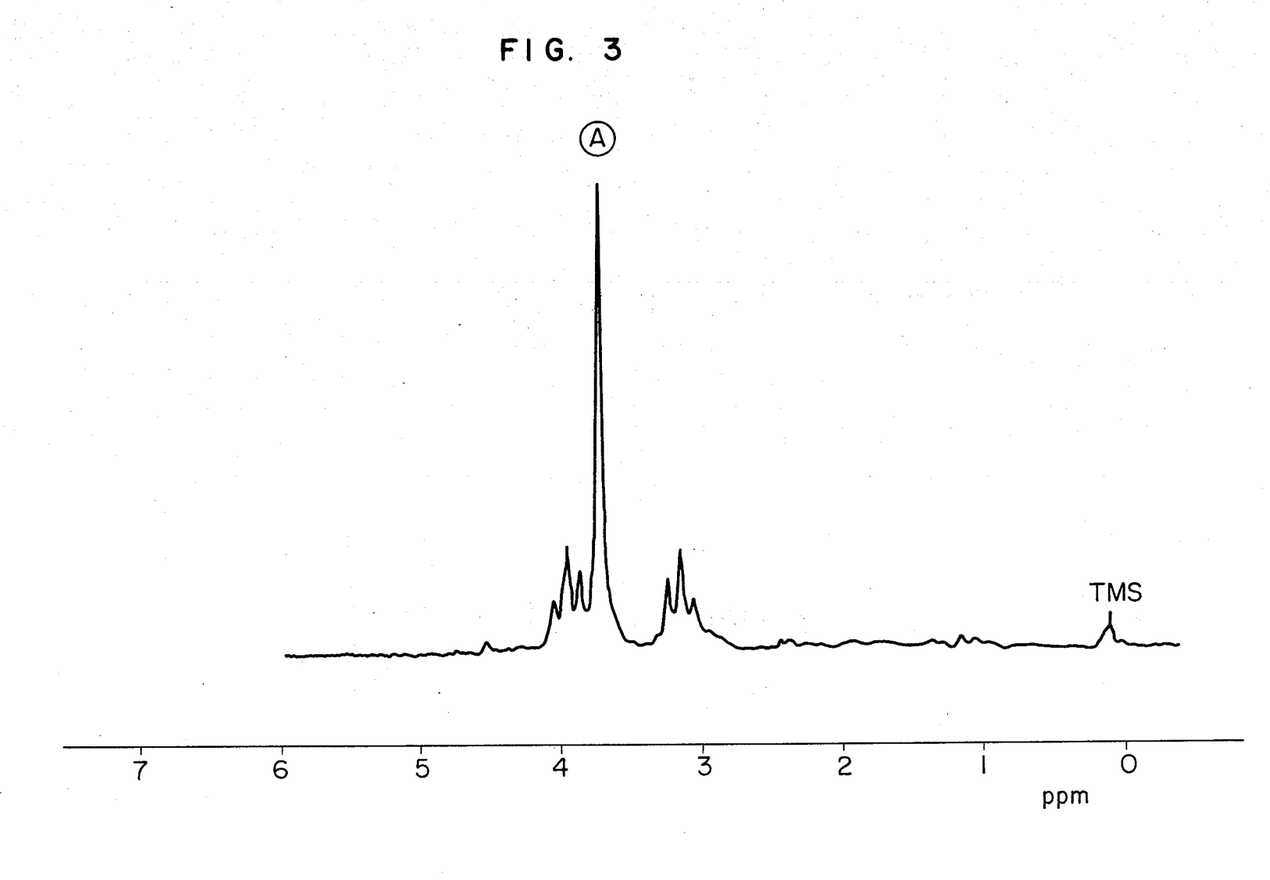
FIG. 3 is the NMR spectrum of said compound.

The NMR spectrum of the reaction product is shown in FIG. 3. In the cyclic trisulfide represented by the formula, the chemical shift (A) of the proton attached to the d carbon is on the higher magnetic field side than the chemical shift of the proton attached to the c carbon atom.

Figure 4:
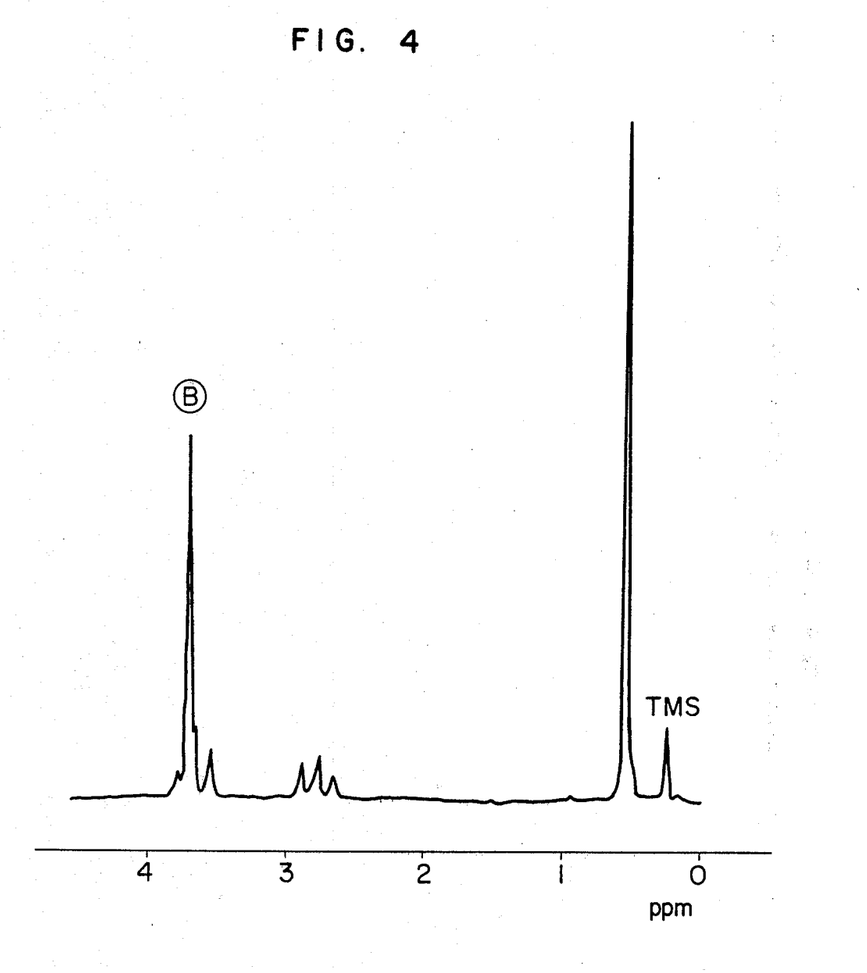
FIG. 4 is the NMR spectrum of α,ω-3,6,9-trioxaundecanebistrimethylsilyl sulfide.

The NMr spectrum of the linear silyl sulfide represented by the formula, is shown in FIG. 4, in which the chemical shift (B) of the proton attached to the d carbon is observed on the lower magnetic field side than the chemical shift of the proton attached to the c carbon.

It is clear from FIGS. 3 and 4 that the reaction product is a cyclic sulfur compound.

It is determined from the mass spectrometric analysis that the parent peak is 256, and this accords with the molecular weight of 1,2,3-trithia-6,9,12-trioxatetradecane.

Figure 5:
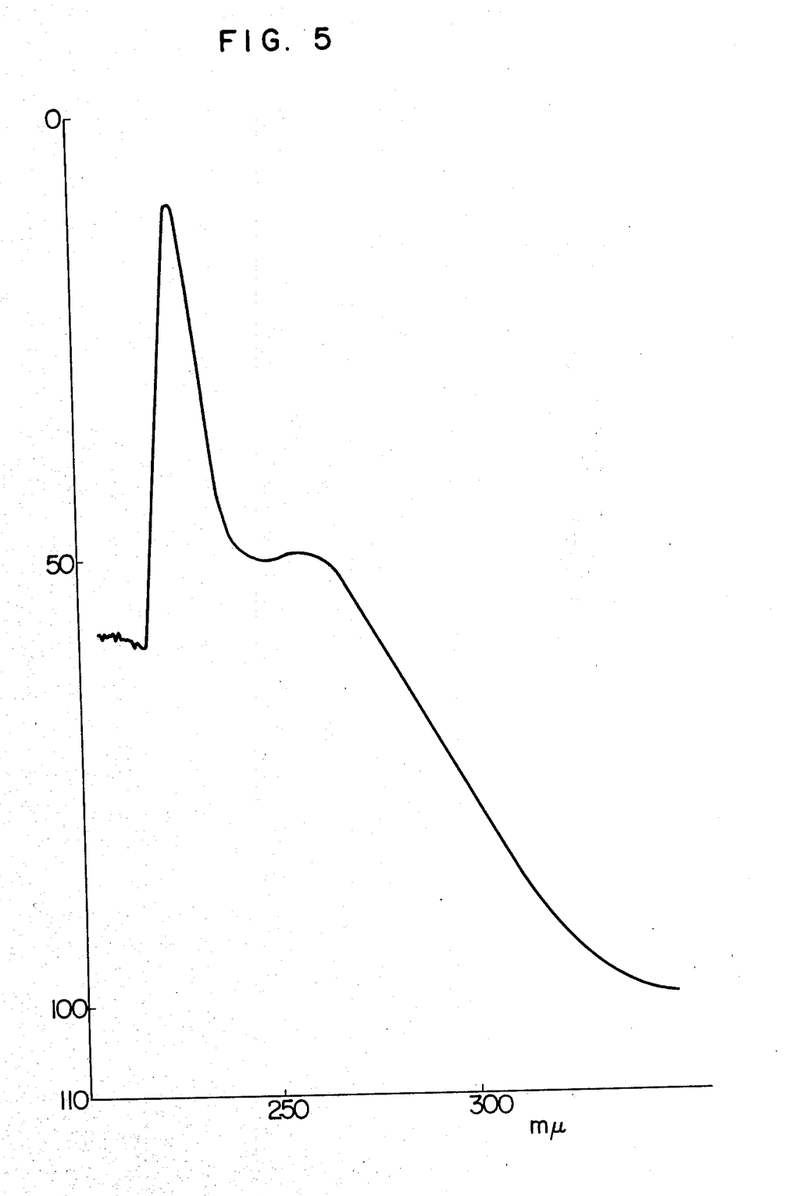
FIG. 5 is the UV spectrum of said compound.

The UV spectrum of 1,2,3-trithia-6,9,12-trioxatetradecane is shown in FIG. 5, from which it can be seen that the maximum absorption wavelength is shifted to the long wavelength side as compared with the S$_2$ compound, and the absorption coefficient $\epsilon$ is also greater.

EXAMPLE 2

The same procedure as in Example 1 was repeated, except that HS$+$CH$_2$CH$_2$O$)_2$CH$_2$CH$_2$SH or HSCH$_2$CH$_2$OCH$_2$CH$_2$SH was substituted for the dithiol, to obtain 1,2,3-trithia-6,9-dioxacycloundecane which is a 11-membered ring compound represented by the formula, or 1,2,3-trithia-6-oxacyclooctane which is a 8-membered ring compound represented by the formula, respectively. The results obtained are shown in Table 1.

TABLE 1

| Ring member | —R— | Yield (%) |
|---|---|---|
| 8 | —CH$_2$CH$_2$OCH$_2$CH$_2$— | 41 |
| 11 | $+$CH$_2$CH$_2$O$)_2$CH$_2$CH$_2$— | 43 |

Figure 7:
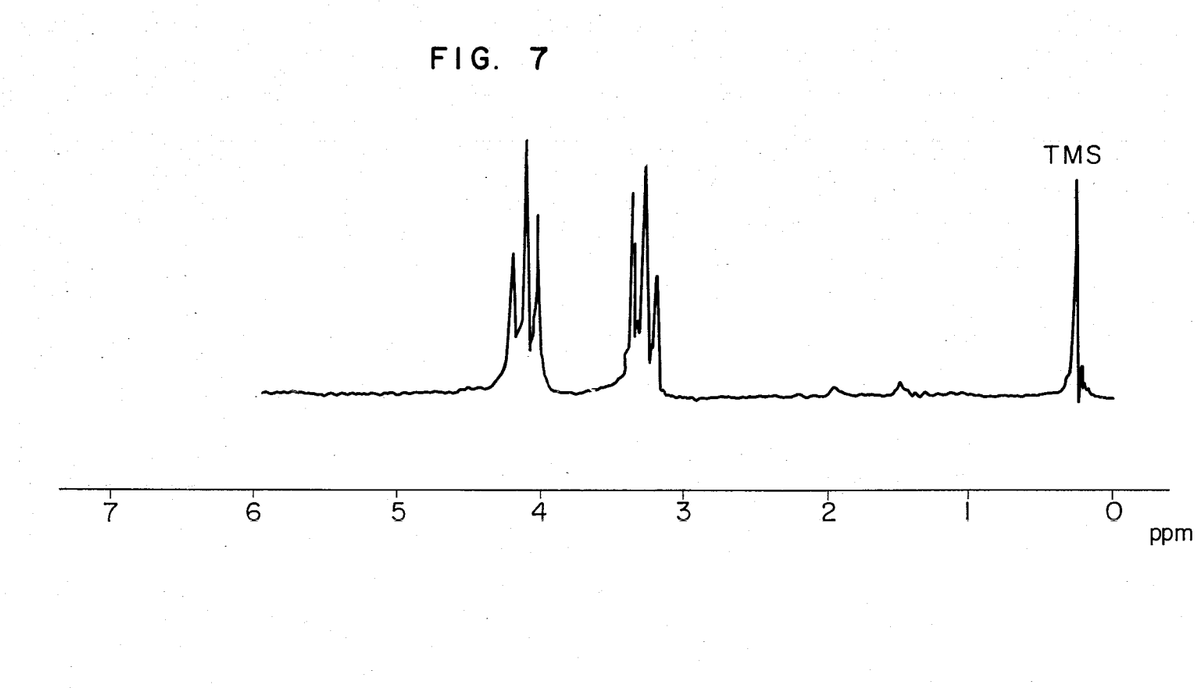
FIG. 7 is the NMR spectrum of said compound.
Figure 8:
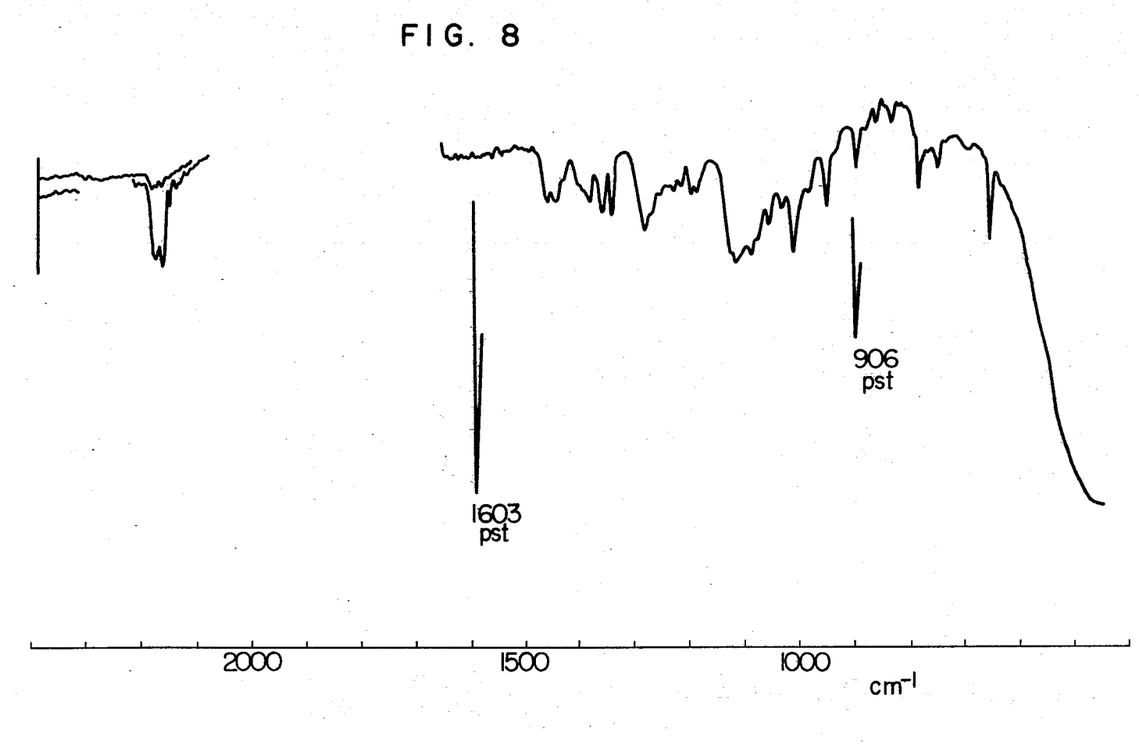
FIG. 8 is the IR spectrum of 1,2,3-trithia-6,9-dioxacloundecan produced in Example 2.
Figure 9:
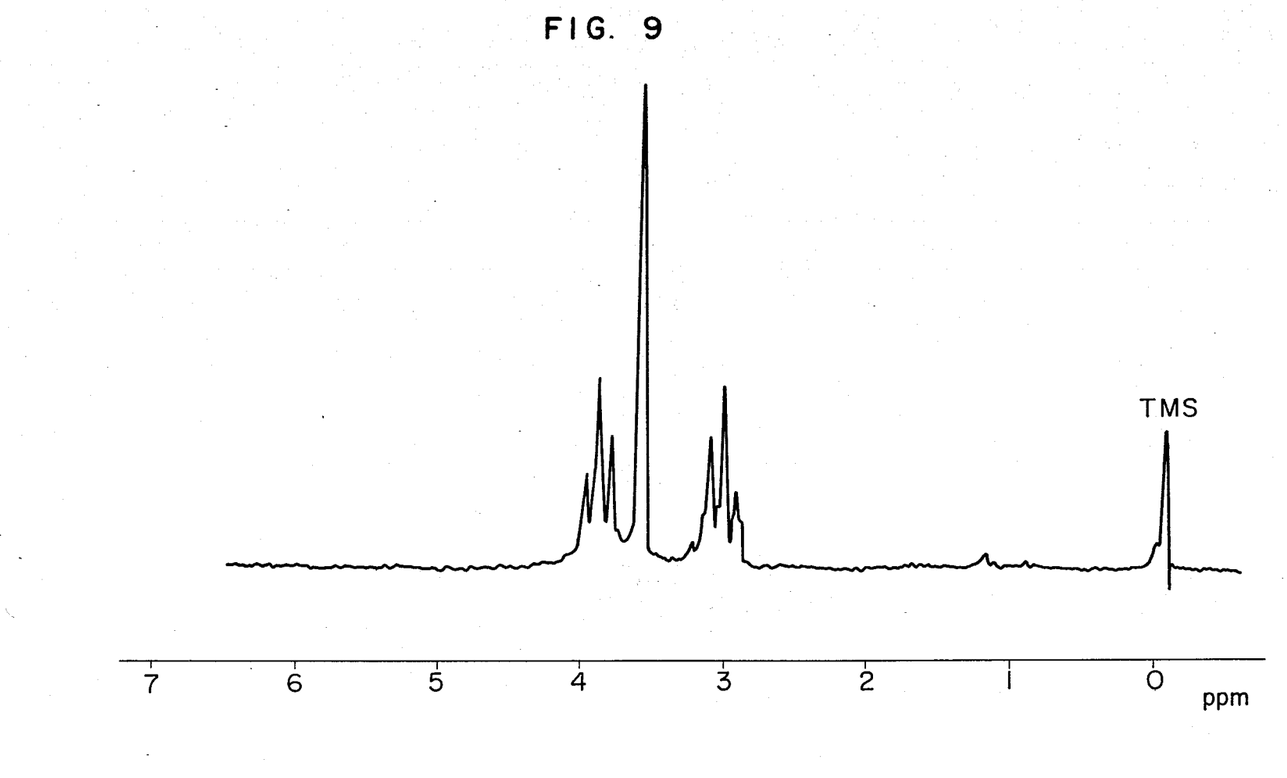
FIG. 9 is the NMR spectrum of said compound.

The IR spectrum and NMR spectrum of the 8-membered ring cyclic sulfur compound are shown in FIGS. 6 and 7, respectively, and the IR spectrum and NMR spectrum of the 11-membered ring cyclic sulfur compound are shown in FIGS. 8 and 9, respectively.

As a result of the mass spectrometric analysis, it was determined that the parent peak of the 8-membered ring compound was 168 and the parent peak of the 11-membered ring compound was 212.

EXAMPLE 3

The same procedure as in Example 1 was repeated, except that bromine was substituted for the sulfur dichloride, to obtain 1,2-dithia-5,8,11-trioxacyclotridecane which is a 13-membered ring compound represented by the formula, Said cyclic sulfur compound (VIII) was oily and the yield thereof was 45%.

Figure 10:
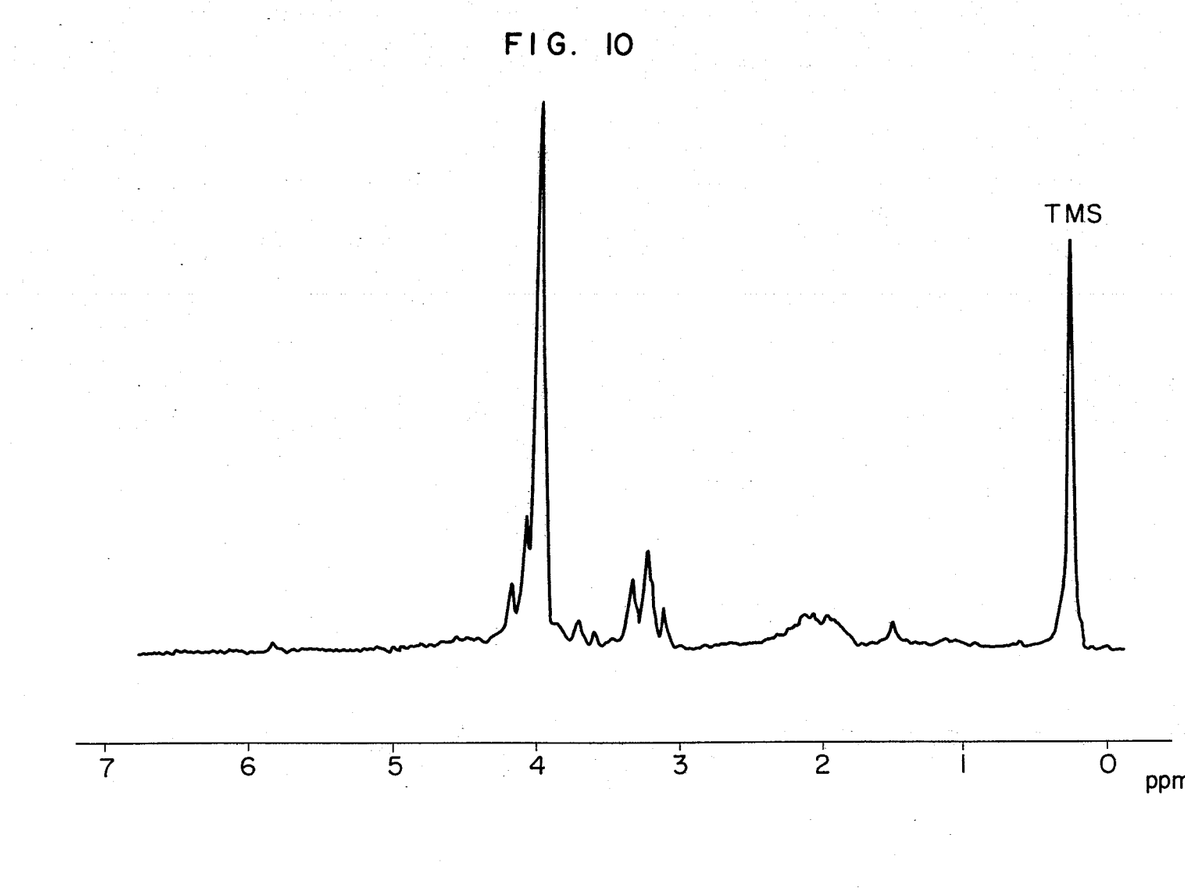
FIG. 10 is the NMR spectrum of 1,2-dithia-5,8,11-trioxacyclotridecane produced in Example 3.

The NMR spectrum of said compound is shown in FIG. 10. The parent peak determined by the mass spectrometric analysis was 224, which accorded with the molecular weight of 1,2-dithia-5,8,11-trioxacyclotridecane.

Figure 11:
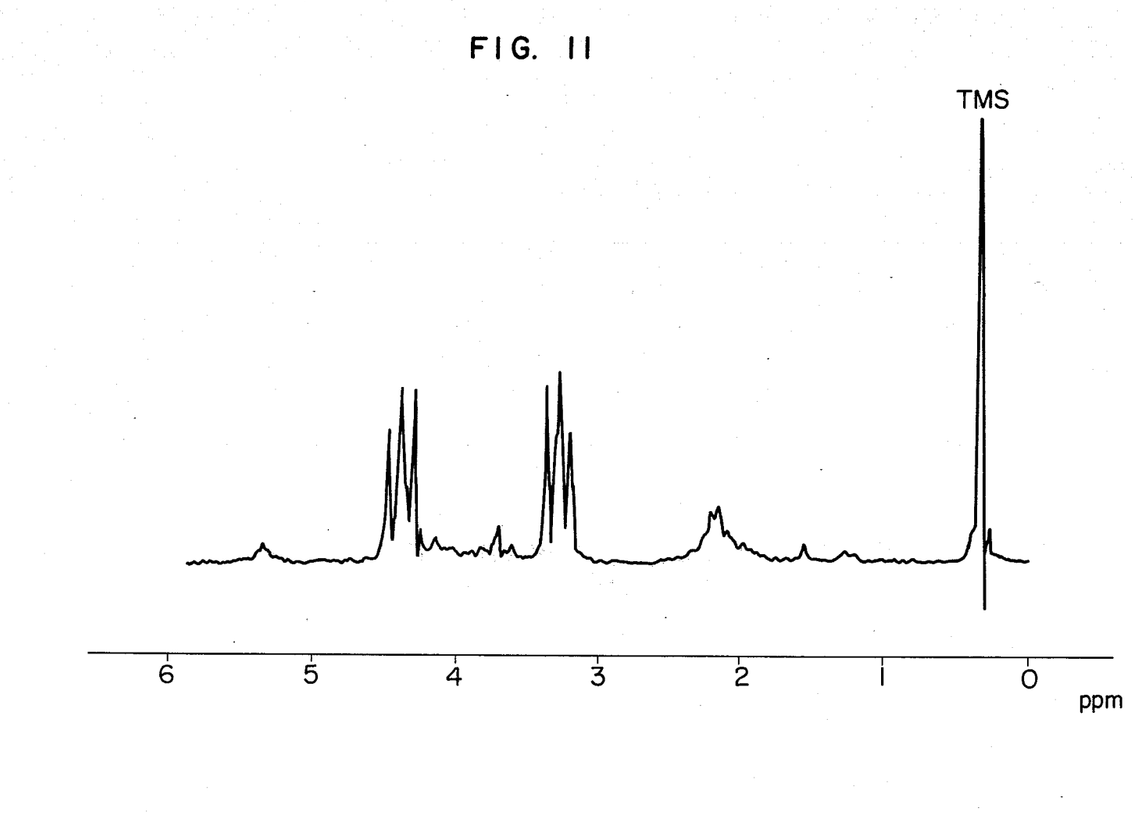
FIG. 11 is the NMR spectrum of 1,2-dithia-5-oxacycloheptane produced in Example 3.

The same procedure as above was repeated, except that HSCH$_2$CH$_2$OCH$_2$CH$_2$SH was substituted for the dithiol, to obtain 1,2-dithia-5-oxacycloheptane which is a 7-membered ring compound represented by the formula, (IX)

and the yield thereof was 46%. The NMR spectrum of said compound is shown in FIG. 11. The parent peak determined by the mass spectrometric analysis was 136.

EXAMPLE 4

The same procedure as in Example 1 was repeated, except that HS—(CH$_2$CH$_2$O)$_2$CH$_2$CH$_2$SH and sulfur monochloride (S$_2$Cl$_2$) were substituted for the dithiol and the sulfur dichloride, respectively, to obtain 1,2,3,4-tetrathia-7,10-dioxacyclododecane which is a 12-membered ring compound represented by the formula, (X)

Further, the same procedure as in Example 1 was repeated, except that sulfur monochloride was substituted for the sulfur dichloride to obtain 1,2,3,4-tetrathia-7,10,13-trioxacyclopentadecane which is a 15-membered ring compound represented by the formula, (XI)

The results obtained are shown in Table 2.

TABLE 2

| Ring member | —R— | Yield (%) |
| --- | --- | --- |
| 12 | —(CH$_2$CH$_2$O)$_2$CH$_2$CH$_2$— | 42 |
| 15 | —(CH$_2$CH$_2$O)$_3$CH$_2$CH$_2$— | 74 |

Figure 12:
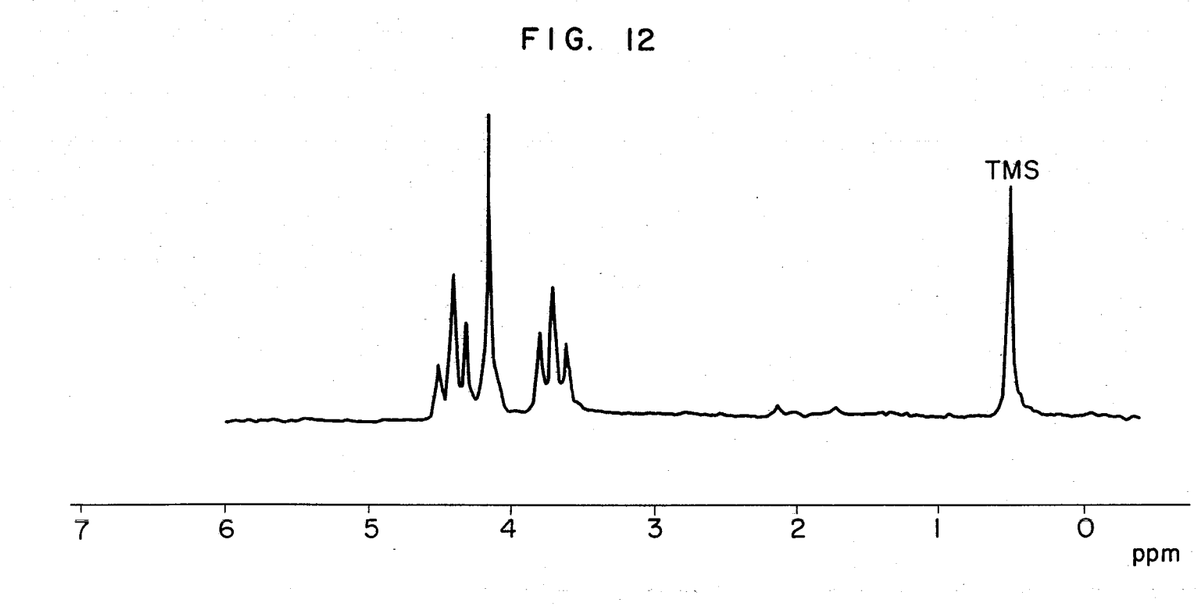
FIG. 12 is the NMR spectrum of 1,2,3,4-tetrathia-7,10-dioxacyclododecane produced in Example 4.
Figure 13:
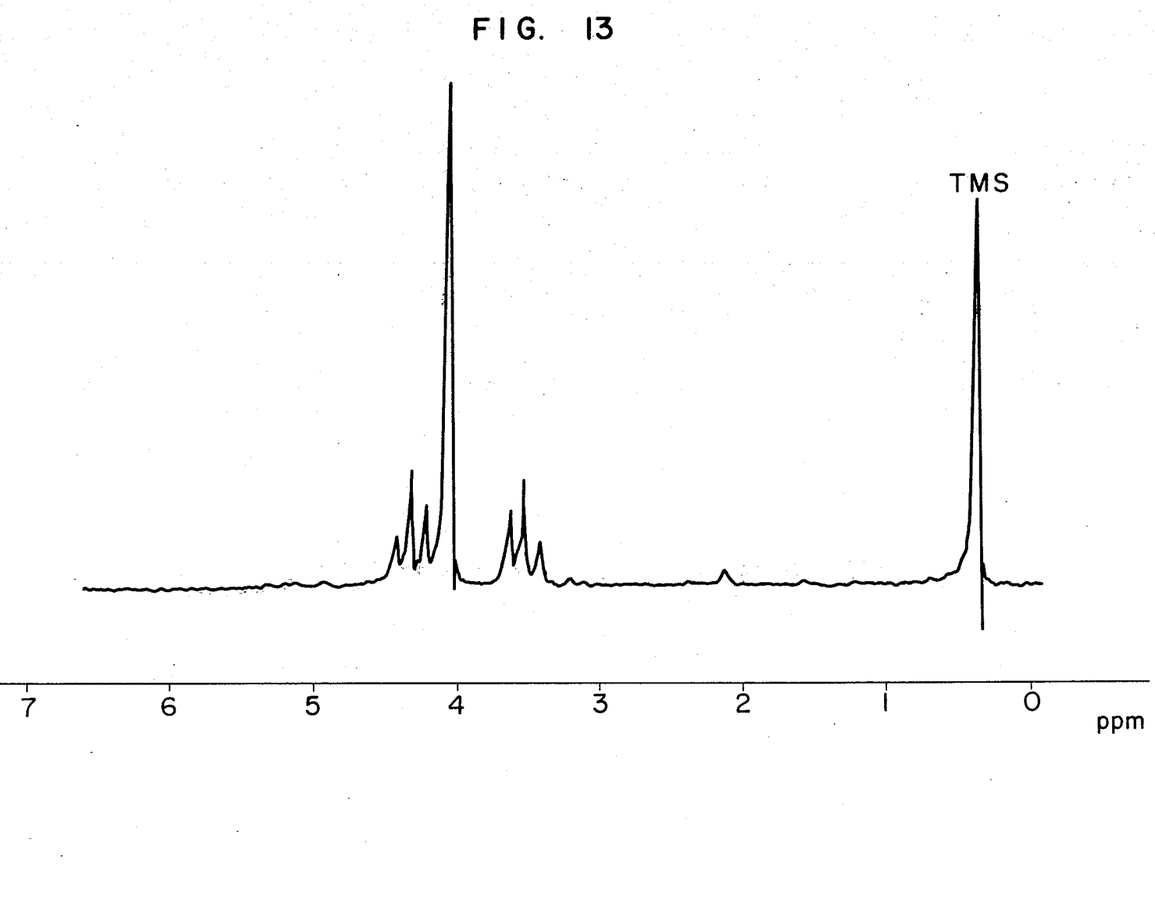
FIG. 13 is the NMr spectrum of 1,2,3,4-tetrathia-7,10,13-trioxacyclopentadecane produced in Example 4. In the measurement of each of the above NMR spectra, the standard material trimethylsilane (TMS) has been added.

The NMR spectrum of the 12-membered ring compound (X) is shown in FIG. 12, and the NMR spectrum of the 15-membered ring compound (XI) is shown in FIG. 13.

As a result of mass spectrometric analysis, the parent peak of the compound (X) was 244 and the parent peak of the compound (XI) was 288.

EXAMPLE 5

α,ω-3,6,9-Trioxaundecanedithiol was reacted with dimethyldichlorosilane to obtain a compound represented by the formula, (XII)

wherein R is —(CH$_2$CH$_2$O)$_3$CH$_2$CH$_2$—, and this compound was then reacted with sulfur monochloride to obtain 1,2,3,4-tetrathia-7,10,13-trioxacyclopentadecane which is a 15-membered ring compound represented by the formula (XI) in a yield of 70%.

EXAMPLE 6

The same procedure as in Example 1 was repeated, except that trimethylchlorotin was substituted for the trimethylchlorosilane to obtain a cyclic sulfur compound represented by the formula (IV).

The same procedure as above was repeated, except that bromine or sulfur monochloride was substituted for the sulfur dichloride to obtain a cyclic sulfur compound represented by the formula (VIII) or (XI), respectively.

The results obtained are shown in Table 3.

TABLE 3

| | Cyclic sulfur compound | Yield (%) |
| --- | --- | --- |
| Bromine | Formula (VIII) | 41 |
| Sulfur dichloride | Formula (IV) | 57 |
| Sulfur monochloride | Formula (XI) | 66 |

EXAMPLE 7

The same procedure as in Example 5 was repeated, except that dimethyldichlorotin was substituted for the dimethyldichlorosilane to obtain 1,2,3,4-tetrathia-7,10,13-trioxacyclopentadecane which is a 15-membered ring compound represented by the formula (XI) in a yield of 54%.

What is claimed is:

1. A cyclic sulfur compound represented by the formula, (I)

wherein R is —(CH$_2$CH$_2$O)$_n$CH$_2$CH$_2$—, m is an integer of 3 or 4 and n is an integer of 1 to 3.

2. A cyclic sulfur compound according to claim 1, wherein the compound has the structural formula,

3. A cyclic sulfur compound according to claim 1, wherein the compound has the structural formula,

4. A cyclic sulfur compound according to claim 1, wherein the compound has the structural formula, 5. A cyclic sulfur compound according to claim 1, wherein the compound has the structural formula, 6. A cyclic sulfur compound according to claim 1, wherein the compound has the structural formula,

* * * * *